United States Patent
Goldman

(10) Patent No.: US 11,666,265 B2
(45) Date of Patent: *Jun. 6, 2023

(54) HEARING SYSTEM WITH HEART CONDITION ALERT AND RELATED METHODS

(71) Applicant: GN HEARING A/S, Ballerup (DK)

(72) Inventor: Tomasz Goldman, Hellerup (DK)

(73) Assignee: GN HEARING A/S, Ballerup (DK)

( * ) Notice: Subject to any disclaimer, the term of this patent is extended or adjusted under 35 U.S.C. 154(b) by 655 days.

This patent is subject to a terminal disclaimer.

(21) Appl. No.: 16/600,870

(22) Filed: Oct. 14, 2019

(65) Prior Publication Data
US 2020/0138315 A1    May 7, 2020

(30) Foreign Application Priority Data
Nov. 5, 2018   (EP) .................................... 18204468

(51) Int. Cl.
*A61B 5/361*     (2021.01)
*H04R 25/00*     (2006.01)
(Continued)

(52) U.S. Cl.
CPC ............. *A61B 5/361* (2021.01); *A61B 5/11* (2013.01); *A61B 5/6817* (2013.01); *A61B 5/742* (2013.01);
(Continued)

(58) Field of Classification Search
CPC ... A61B 5/02438; A61B 5/361; A61B 5/6815; A61B 5/6817; H04R 2225/025; H04R 2225/55
See application file for complete search history.

(56) References Cited

U.S. PATENT DOCUMENTS 10,398,381 B1 *  9/2019  Heneghan ............ A61B 5/0261
2006/0161208 A1 *  7/2006  Pastore .............. A61N 1/36592
                                                              607/17
(Continued)

FOREIGN PATENT DOCUMENTS

CN          205493807           8/2016
EP          3313092              4/2018
(Continued)

OTHER PUBLICATIONS

Extended European Search Report dated May 6, 2019 for corresponding European Application No. 18204468.5.
(Continued)

*Primary Examiner* — Carl H Layno
*Assistant Examiner* — Manolis Pahakis
(74) *Attorney, Agent, or Firm* — Vista IP Law Group, LLP

(57) ABSTRACT

A hearing device includes: a first microphone configured to provide a first input signal; a first processor unit configured to provide a processed signal based on the first input signal to compensate for a hearing loss of a user of the first hearing device; a receiver configured to output sound based on the processed signal; and a first sensor configured to provide a first sensor signal for detecting an atrial fibrillation condition of the user. An electronic device includes: a communication interface configured to communicate with a hearing device; and a processing unit configured to obtain, via the communication interface, information associated with an atrial fibrillation condition of a user, the information comprising a sensor data transmitted from the hearing device and/or information indicating the atrial fibrillation condition detected based on the sensor data; wherein the accessory device is configured to output a signal indicative of the atrial fibrillation condition.

43 Claims, 6 Drawing Sheets

(51) Int. Cl.
*A61B 5/11* (2006.01)
*A61B 5/00* (2006.01)
(52) U.S. Cl.
CPC .......... *A61B 5/7475* (2013.01); *H04R 25/55* (2013.01); *H04R 25/604* (2013.01); *H04R 25/609* (2019.05); *H04R 25/652* (2013.01); *H04R 2225/025* (2013.01); *H04R 2225/55* (2013.01)

(56) References Cited

U.S. PATENT DOCUMENTS

| | | | | |
|---|---|---|---|---|
| 2006/0161209 A1* | 7/2006 | Pastore | ................. | A61N 1/365 607/17 |
| 2006/0161210 A1* | 7/2006 | Pastore | ............. | A61N 1/36592 607/17 |
| 2010/0174205 A1* | 7/2010 | Wegerif | ............ | A61B 5/02405 600/515 |
| 2012/0103337 A1* | 5/2012 | Avni | ..................... | A61M 21/02 128/204.23 |
| 2015/0305634 A1* | 10/2015 | Stergiou | ............ | A61B 5/02405 600/509 |
| 2016/0256060 A1* | 9/2016 | Katra | .................... | A61N 1/395 |
| 2016/0331247 A1* | 11/2016 | Albert | .................. | A61B 5/681 |
| 2017/0007129 A1* | 1/2017 | Kaib | .................... | A61N 1/3968 |
| 2017/0112447 A1* | 4/2017 | Aumer | .................. | A61B 5/721 |
| 2017/0325700 A1* | 11/2017 | Lane | ................. | A61N 1/36053 |
| 2018/0014741 A1* | 1/2018 | Chou | .................. | A61B 5/6803 |
| 2018/0199893 A1* | 7/2018 | Hübner | ................ | A61B 5/0816 |
| 2018/0250510 A1* | 9/2018 | Ziv | ...................... | A61N 1/0476 |
| 2018/0263562 A1* | 9/2018 | Laplante-Lévesque | ..................... | H04R 25/552 |
| 2018/0333056 A1* | 11/2018 | Chou | .................. | A61B 5/6824 |
| 2019/0001131 A1* | 1/2019 | Ziv | .................... | A61N 1/36031 |
| 2019/0065777 A1* | 2/2019 | Ravuvari | ................ | G06F 21/32 |
| 2019/0328306 A1* | 10/2019 | Gluckman | ............ | A61B 5/316 |
| 2019/0373377 A1* | 12/2019 | Larsen | ................ | A61B 5/1118 |
| 2020/0138299 A1* | 5/2020 | Goldman | ............ | A61B 5/0002 |
| 2020/0324105 A1* | 10/2020 | Po | ...................... | A61B 5/02416 |
| 2020/0375480 A1* | 12/2020 | Costa | ..................... | A61B 5/024 |
| 2021/0290175 A1* | 9/2021 | Jayaraman | ............ | G16H 50/20 |
| 2021/0345896 A1* | 11/2021 | Moore | ................ | A61B 5/6826 |
| 2021/0345897 A1* | 11/2021 | Moore | ................ | A61B 5/6831 |

FOREIGN PATENT DOCUMENTS

| | | | | |
|---|---|---|---|---|
| WO | WO 2015/121689 A1 | 8/2015 | | |
| WO | WO 2016/061381 A1 | 4/2016 | | |
| WO | WO 2016/120870 A1 | 8/2016 | | |
| WO | WO 2017/011431 A2 | 1/2017 | | |
| WO | WO-2017011431 A2 * | 1/2017 | .......... | A61B 5/0022 |
| WO | WO 2018175196 | 9/2018 | | |

OTHER PUBLICATIONS

European Examination Report dated Jun. 28, 2021 for European Patent Application No. 18204468.5.

* cited by examiner

HEARING SYSTEM WITH HEART CONDITION ALERT AND RELATED METHODS

RELATED APPLICATION DATA

This application claims priority to, and the benefit of, European Patent Application No. 18204468.5 filed on Nov. 5, 2018. The entire disclosure of the above application is expressly incorporated by reference herein.

FIELD

The present disclosure relates to a hearing system, hearing device, accessory device, and related methods including methods of operating a hearing system device.

BACKGROUND

Almost a quarter of persons with atrial fibrillation (AFib) are not aware that they have AFib due to a lack of symptoms. Detection of AFib requires precise monitoring of the heart rate and heart rate variations, preferably over long periods of time.

SUMMARY

Accordingly, there is a need for precise and reliable determination and/or communication of heart conditions and in particular AFib.

Methods of operating a hearing system comprising a first hearing device and one or both of a second hearing device and an accessory device are disclosed.

Further, a hearing system is disclosed, the hearing system comprising a first hearing device and one or both of a second hearing device and an accessory device.

A method of operating a hearing system comprising a first hearing device and an accessory device is disclosed, the method comprising obtaining sensor data, the sensor data comprising first sensor data indicative of a first sensor signal from the first hearing device arranged at a first ear of a user; detecting an atrial fibrillation condition of the user based on the first sensor data; and in accordance with detecting the atrial fibrillation condition, outputting a first output signal indicative of the atrial fibrillation condition.

Also disclosed is a haring system comprising a first hearing device and an accessory device, wherein the hearing system is configured to perform a method of operating a hearing system comprising a first hearing device and an accessory device as disclosed herein.

Also disclosed is a method of operating a hearing system comprising a first hearing device and a second hearing device, the method comprising obtaining sensor data, the sensor data comprising first sensor data representing first physiological data and second sensor data representing second physiological data, where the first sensor data is indicative of first sensor signal from the first hearing device arranged at a first ear of a user, and the second sensor data is indicative of second sensor signal from the second hearing device arranged at a second ear of the user; comparing the first sensor data and the second sensor data; identifying a first parameter based on the comparison of the first sensor data and the second sensor data; and outputting a first output signal indicative of the first parameter.

Further, a hearing system is disclosed, the hearing system comprising a first hearing device comprising a first sensor for obtaining first sensor data; a second hearing device comprising a second sensor for obtaining second sensor data; a processing unit, e.g. as part of a processor unit of the first hearing device or as part of a processing unit of an accessory device, configured to compare the first sensor data and the second sensor data; identify a first parameter based on the comparison of the first sensor data and the second sensor data; and output a first output signal indicative of the first parameter.

It is an important advantage of the present disclosure that hearing device(s) is/are used for detecting and monitoring heart conditions of a user. A hearing device is typically worn for long periods of time, typically all day, which is advantageous in particular for detection of atrial fibrillation (AFIB) or other heart conditions.

Further, the present methods and devices/systems provide an improved detection and/or monitoring of heart conditions through more reliable an accurate detection of physiological parameters of a user.

The present disclosure enables real-time monitoring and effective communication of heart-rate conditions enabling a user to react fast and effectively to the occurrence of AFib.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
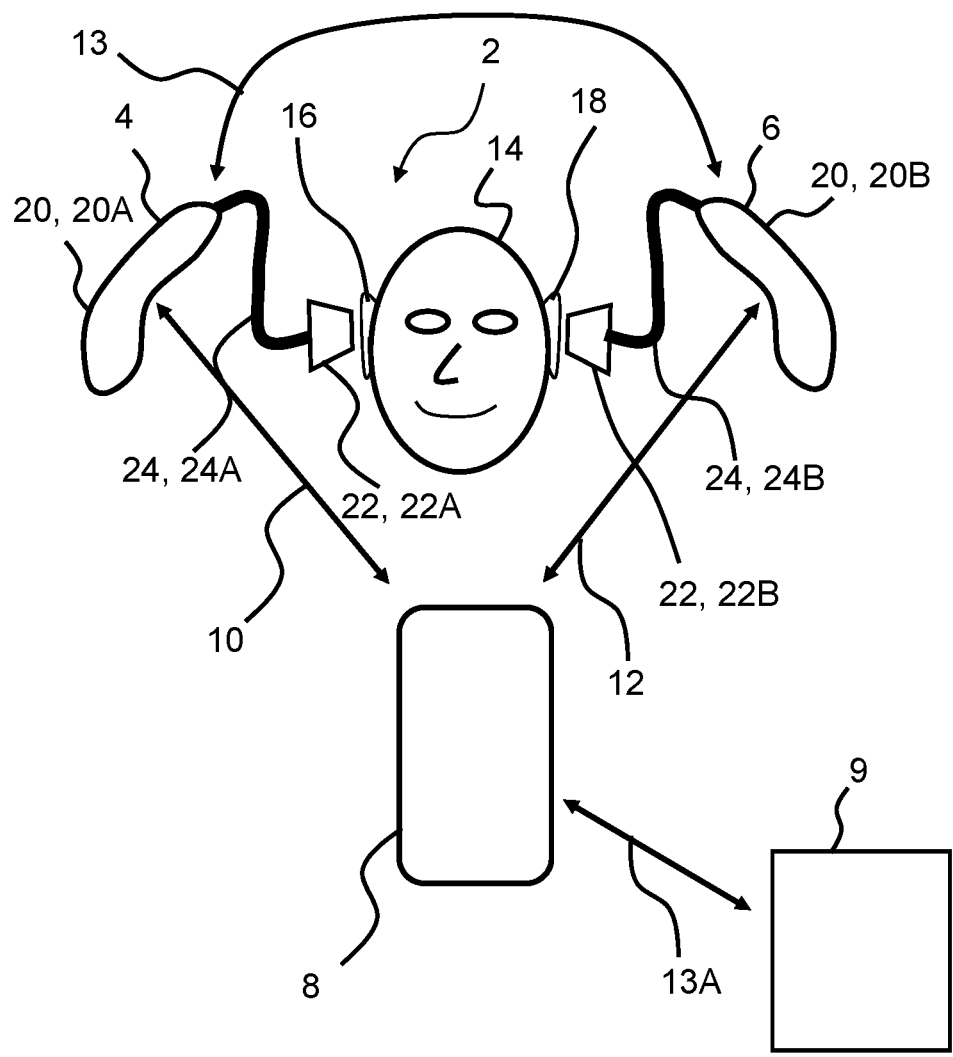
FIG. 1 schematically illustrates an exemplary hearing system according to the present disclosure.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The present disclosure relates to a hearing system and devices thereof, such as a first hearing device and/or a second hearing device.

Hearing device(s), such as first hearing device and/or second hearing device, are disclosed. In the present context, references to "the hearing device" refers to a first hearing device and/or to a second hearing device. The hearing device may be a hearable or a hearing aid, wherein the processor is configured to compensate for a hearing loss of a user. The hearing device may be of the behind-the-ear (BTE) type, in-the-ear (ITE) type, in-the-canal (ITC) type, receiver-in-canal (RIC) type or receiver-in-the-ear (RITE) type. The hearing aid may be a binaural hearing aid.

The hearing device may be configured for wireless communication with one or more devices, such as with another hearing device, e.g. as part of a binaural hearing system, and/or with one or more accessory devices, such as a smartphone and/or a smart watch.

The hearing device, such as the first hearing device and/or the second hearing device, optionally comprises a set of microphones. The set of microphones may comprise one or more microphones. The set of microphones comprises a first microphone for provision of a first microphone input signal and/or a second microphone for provision of a second microphone input signal. The set of microphones may comprise N microphones for provision of N microphone signals, wherein N is an integer in the range from 1 to 10. In one or more exemplary hearing devices, the number N of microphones is two, three, four, five or more. The set of microphones may comprise a third microphone for provision of a third microphone input signal.

The first hearing device may comprise a first microphone and a first processor unit. The first microphone may be arranged in a BTE housing of the first hearing device or in an ear canal part/earpiece of the first hearing device. The first processor unit may be arranged in a BTE housing of the first hearing device or in an ear canal part/earpiece of the first hearing device.

The first hearing device may comprise a first sensor configured for providing the first sensor signal. The first sensor may be a photoplethysmogram sensor. The first sensor may be configured for being positioned in the concha or in an ear canal of the user. In other words, a first sensor providing the first sensor signal may be a photoplethysmogram sensor. The first sensor may be communicatively coupled to the first hearing device/first processor unit via a second cable comprising a plurality of electrical wires.

The hearing system, such as the first hearing device, may comprise a first receiver. The first receiver may be arranged or positioned at least partly in an ear canal of the user. The first receiver may be communicatively coupled to the first processor unit of the first hearing device via a first cable comprising a plurality of electrical wires, e.g. in a BTE-RIE hearing device or a BTE-MARIE hearing device.

In one or more exemplary methods/hearing systems, the first receiver and the first sensor are contained in a housing of the first hearing device in the ear canal of the user. In one or more exemplary methods/hearing devices, the first receiver and the first sensor are contained in an ear piece of the hearing device, e.g. where the first hearing device is a BTE-RIE hearing device, a BTE-MARIE hearing device, or a ITE hearing device.

The first hearing device may comprise a motion sensor also denoted first motion sensor. The first motion sensor delivers a first motion sensor signal for provision of first motion data. In other words, first motion data is measured using a first motion sensor arranged in the first hearing device.

The second hearing device may comprise a second microphone and a second processor unit. The second microphone may be arranged in a BTE housing of the second hearing device or in an ear canal part/earpiece of the second hearing device. The second processor unit may be arranged in a BTE housing of the second hearing device or in an ear canal part/earpiece of the second hearing device.

The hearing system, such as the second hearing device, may comprise a second sensor configured for providing the second sensor signal. The second sensor may be a photoplethysmogram sensor. The second sensor may be configured for being positioned in a concha or in an ear canal of the user. In other words, a second sensor providing the second sensor signal may be a photoplethysmogram sensor.

The second hearing device may comprise a second receiver. The second receiver may be arranged or positioned at least partly in an ear canal of the user. The second receiver may be communicatively coupled to the second processor unit of the second hearing device via a second cable comprising a plurality of electrical wires, e.g. in a BTE-RIE hearing device or a BTE-MARIE hearing device.

In one or more exemplary methods/hearing systems, the second receiver and the second sensor are contained in a housing in the ear canal of the user. In one or more exemplary methods/hearing devices, the second receiver and the second sensor are contained in an ear piece of the hearing device.

The second hearing device may comprise a motion sensor also denoted second motion sensor. The second motion sensor delivers a second motion sensor signal for provision of second motion data. In other words, second motion data is measured using a second motion sensor arranged in the second hearing device.

The hearing system may comprise an accessory device. An accessory device (also referred to as an external device) may be a mobile phone or other handheld device. An accessory device may be a personal electronic device, e.g. a wearable, such as a watch or other wrist-worn electronic device. The accessory device may be a tablet computer.

The methods disclosed herein comprises obtaining sensor data, the sensor data comprising first sensor data, e.g. representing first physiological data. The sensor data may comprise second sensor data, e.g. representing second physiological data.

The first physiological data and the second physiological data may be representative of a heart function of a user.

The first sensor data are indicative of a first sensor signal from the first hearing device arranged at a first ear of a user.

The second sensor data are indicative of a second sensor signal from the second hearing device arranged at a second ear of a user. Accordingly, in one or more exemplary methods, the hearing system comprises a second hearing device, wherein the sensor data comprises second sensor data indicative of a second sensor signal from the second hearing device arranged at a second ear of the user.

The sensor data may be obtained over a time period of more than 30 seconds, preferably more than 60 seconds, preferably more than 90 seconds, preferably 120 seconds. In one or more exemplary methods, sensor data are obtained for one or a plurality of time periods, such as for a primary time period and/or a secondary time period.

In one or more exemplary methods, the method comprises detecting an atrial fibrillation condition of the user based on the first sensor data and/or based on the second sensor data; and in accordance with detecting the atrial fibrillation condition, outputting a first output signal indicative of the atrial fibrillation condition. Detecting the atrial fibrillation condition based on sensors data from different hearing devices allows for more accurate and/or failsafe determination of the atrial fibrillation condition, e.g. leading to a reduced number of false positives, i.e. erroneous determination of presence of AFib. Detecting an atrial fibrillation condition may comprise selecting the atrial fibrillation condition from a plurality of atrial fibrillation conditions, such as from at least 3 atrial fibrillation conditions, at least 4 atrial fibrillation conditions, or at least 5 atrial fibrillation conditions.

In one or more exemplary methods, the method comprises comparing, e.g. in the first hearing device and/or in an accessory device, the first sensor data and the second sensor data; identifying a first parameter based on the comparison of the first sensor data and the second sensor data; and outputting a first output signal indicative of the first parameter.

In one or more exemplary method, comparing the first sensor data and the second sensor data may comprise comparing periods of the first sensor data and the second sensor data and, in accordance with a first selection criterion being satisfied, selecting the first sensor data (or weighted first sensor data) as output sensor data (for the periods where the first selection criterion is satisfied); and wherein identifying a first parameter based on the comparison of the first sensor data and the second sensor data is based on the output sensor data. Comparing the first sensor data and the second sensor data may comprise, in accordance with a common selection criterion being satisfied, selecting a combination of the first sensor data (or weighted first sensor data) and the second sensor data (or weighted second sensor data) as output sensor data (for the periods where the common selection criterion is satisfied). Comparing the first sensor data and the second sensor data may comprise, in accordance with a second selection criterion being satisfied, selecting the second sensor (or weighted second sensor data) data as output sensor data (for the periods where the second selection criterion is satisfied). Accordingly, comparing the first sensor data and the second sensor data may comprise determining sensor output data, and identifying a first parameter based on the sensor output data.

In one or more exemplary methods, comparing the first sensor data and the second sensor data comprises identifying primary time periods of the first and the second sensor data, respectively, comparing the primary time periods of the first and the second sensor data, and identifying the first parameter based on one or both primary time periods of the first and the second sensor data.

In one or more exemplary methods, identifying the first parameter comprises identifying parts of the sensor data that differ from default physiological data.

In one or more exemplary methods, identifying the first parameter comprises identifying parts of the sensor data that have a similarity to a predefined pattern representing a physiological anomaly.

In one or more exemplary methods, identifying the first parameter comprises performing a Heart Rate Variability analysis on the sensor data. Thus, the first parameter may be an output of a Heart Rate Variability analysis.

In one or more exemplary methods, the first parameter is indicative of heart rate variations of the user. The first parameter may be indicative of an atrial fibrillation condition of the user. The first parameter is indicative of one or more R-R intervals of the sensor data.

In one or more exemplary methods, the first parameter comprises a data pattern. The data pattern may be indicative of a physiological anomaly.

In one or more exemplary methods, the method comprises identifying a second parameter based on the first sensor data, the second sensor data and optionally the first parameter, wherein the second parameter is indicative of presence of atrial fibrillation or indicative of an atrial fibrillation condition.

In one or more exemplary methods, outputting a first output signal, e.g. indicative of the atrial fibrillation condition and/or indicative of the first parameter, comprises outputting a first audio signal via the first hearing device. Thus, the user can be warned or informed when the AFib occurs with a high chance of the user hearing the first audio signal since the user wears the first hearing device.

In one or more exemplary methods, the method comprises detecting a user activation of the accessory device; and in accordance with detecting the atrial fibrillation condition and detecting the user activation, outputting a second output signal indicative of the atrial fibrillation condition. The second output signal may be different from the first output signal, the second output signal may be a visual output. Thus, more detailed information on the atrial fibrillation condition may be conveyed to the user in a second output signal. Accordingly, the user is alerted that his attention is needed using the first output signal prompting the user to visit his accessory device with a high chance of being noted by the user, and a second output signal on the accessory device uses the larger processing power and ways of output to provide more detailed information on the atrial fibrillation condition. This in turn provides the user with detailed, fast, and reliable information on the atrial fibrillation condition allowing the user to take the optimum or correct measures to reduce the impact from the occurrence of the atrial fibrillation condition.

In one or more exemplary methods, outputting a second output signal indicative of the atrial fibrillation condition comprises displaying, on a display of the accessory device, a first user interface comprising a first user interface element indicative of the atrial fibrillation condition. The first user interface element may comprise a Poincaré plot, a relative scale, e.g. 1-5, with an indicator of the atrial fibrillation condition, e.g. where 1 indicates very low risk of heart condition and/or where 5 indicates very high risk of heart condition.

In one or more exemplary methods, the method comprises displaying, on the display of the accessory device, a second user interface element indicative of a transmit action; detecting user selection of the second user interface element; and in accordance with detecting user selection of the second user interface element, transmitting the sensor data to a server device. Thereby, a user is able to decide if he/she wishes to share his health data and in which cases. The second user interface element may form a part of the second output signal. Thus, outputting a second output signal indicative of the atrial fibrillation condition may comprise displaying a second user interface element indicative of a transmit action.

In one or more exemplary methods, the method comprises displaying, on the display of the accessory device, a third user interface element indicative of a heart condition measurement with the accessory device; detecting user selection of the third user interface element; and in accordance with detecting user selection of the third user interface, performing a heart condition measurement with the accessory device. The method optionally comprises transmitting a result of the heart condition measurement to a server device. Thereby a user is able to in an effective way verify the atrial fibrillation condition detected by the first sensor/second sensor of the hearing device(s). The third user interface element may form a part of the second output signal. Thus, outputting a second output signal indicative of the atrial fibrillation condition may comprise displaying a third user interface element indicative of a heart condition measurement with the accessory device In one or more exemplary methods, the method comprises outputting user instructions to the user, e.g. by displaying, on the display of the accessory device, a fourth user interface element with user instructions and/or outputting a second audio signal via the first hearing device, wherein the second audio signal is indicative of the user instructions. The fourth user interface element may form a part of the second output signal. Thus, outputting a second output signal may comprise displaying, on the display of the accessory device, a fourth user interface element with user instructions. The method optionally comprises detecting user behaviour of the user; determining if the user behaviour does not correspond to the user instructions; and in accordance with determining that the user behaviour does not correspond to the user instructions, outputting a fifth output signal indicative of non-compliance with the user instructions. Thereby a user is guided through how to react on the AFib condition, and reminded if he/she does not act accordingly.

In one or more exemplary methods, detecting user behaviour of the user is based on the motion data, e.g. the first motion data and/or the second motion data from the first hearing device and/or the second hearing device. Detecting user behaviour may be based on motion data from the accessory device, e.g. from one or more motion sensors of the accessory device. In one or more exemplary methods, the method optionally comprises detecting user behaviour, such as activity/motion, of the user; determining if the user behaviour does not correspond to the user instructions, e.g. by determining if the activity/motion is larger than an activity threshold in contrast to user instructions on resting; and in accordance with determining that the user behaviour does not correspond to the user instructions, e.g. if activity is larger than the activity threshold, outputting a fifth output signal indicative of non-compliance with the user instructions. The fifth output signal may comprise a third audio signal via the first hearing device and/or a fifth user interface element displayed on accessory device display.

In one or more exemplary methods, detecting an atrial fibrillation condition of the user comprises performing Heart Rate Variability analysis on the sensor data. An atrial fibrillation condition may be detected if a first parameter P_1 indicative of heart rate variations meets a first criterion, e.g. if P_>TH_1, where TH_1 is a first threshold.

In one or more exemplary methods, detecting an atrial fibrillation condition of the user comprises determining a plurality of R-R intervals based on the sensor data. The method optionally comprises comparing the R-R intervals. An atrial fibrillation condition may be detected if a difference between the R-R intervals meets a second criterion, e.g. if P_2>TH_2, wherein P_2 is a second parameter indicative of differences between R-R intervals and TH_2 is a second threshold.

In one or more exemplary methods, the method further comprises detecting or receiving a sound input signal by the first microphone for provision of a first input signal; processing by the first processor unit, the first input signal according to a hearing loss of the user wearing the first hearing device; and outputting a processed signal by the first processor unit. In other words, the processed signal is based on the first input signal.

In one or more exemplary methods, the method may comprise, in accordance with detecting the atrial fibrillation condition, forgoing outputting a processed signal by the first processor unit. In other words, the hearing device processing may be halted, paused or stopped when the first hearing device outputs the first output signal, which further increases the chances of the user noticing the first output signal and therefore being able to react on the detection of the atrial fibrillation condition.

In one or more exemplary methods, the method further comprises outputting, with the first receiver, a first audio output signal based on the processed signal.

In one or more exemplary methods, the method further comprises obtaining motion data, such as from the first hearing device and/or the second hearing device. Detecting an atrial fibrillation condition of the user may be based on the motion data.

In one or more exemplary methods, comparing the first sensor data and the second sensor data is based on the motion data, such as based on first motion data from a first motion sensor of the first hearing device and/or second motion data from a second motion sensor of the second hearing device. For example, comparing the first sensor data and the second sensor data may comprise determining a first weight based on the (first) motion data and applying the first weight to the first sensor data. For example, comparing the first sensor data and the second sensor data may comprise determining a second weight based on the (second) motion data and applying the second weight to the second sensor data.

In one or more exemplary methods, the motion data comprises first motion data indicative of a first motion sensor signal from the (first) motion sensor; and wherein detecting an atrial fibrillation condition of the user is based on the first motion data. The motion data may comprise second motion data indicative of a second motion sensor signal from the (second) motion sensor; and wherein detecting an atrial fibrillation condition of the user is based on the second motion data.

In one or more exemplary methods, detecting an atrial fibrillation condition of the user further comprises comparing the first motion data to a first motion threshold, and in accordance with the first motion data satisfying a first motion criterion based on the first motion threshold, conditioning the first sensor data. Detecting an atrial fibrillation condition of the user may comprise comparing the second motion data to a second motion threshold, and in accordance with the second motion data satisfying a second motion criterion based on the second motion threshold, conditioning the second sensor data.

FIG. 1 shows an exemplary hearing system of the present disclosure. The hearing system 2 comprises a first hearing device 4 and optionally a second hearing device 6. Further, an accessory device 8, here illustrated as a smartphone is configured for wireless communication with one or both hearing devices 4, 6 via wireless connections 10, 12 respectively. The hearing devices 4,6 may communicate wirelessly via wireless connection 13. The hearing system 2 optionally comprises server device 9, wherein the accessory device 8 is configured for communication with the server device 9 via wireless and/or wired connection 13A. During use, a user 14 wears hearing devices 4, 6 at respective ears 16, 18, i.e. the first hearing device 4 is arranged at a first ear 16 of the user 14 and the second hearing device is arranged at a second ear 18 of the user 14. The hearing devices 4, 6 are illustrated as being of the behind-the-ear type having a housing 20 configured to be worn behind the ear, an earpiece 22, and a tube connector 24 connecting the housing 20 and the ear piece 22. It is to be understood that the hearing devices disclosed herein may be of the in-the-ear type.

Figure 2:
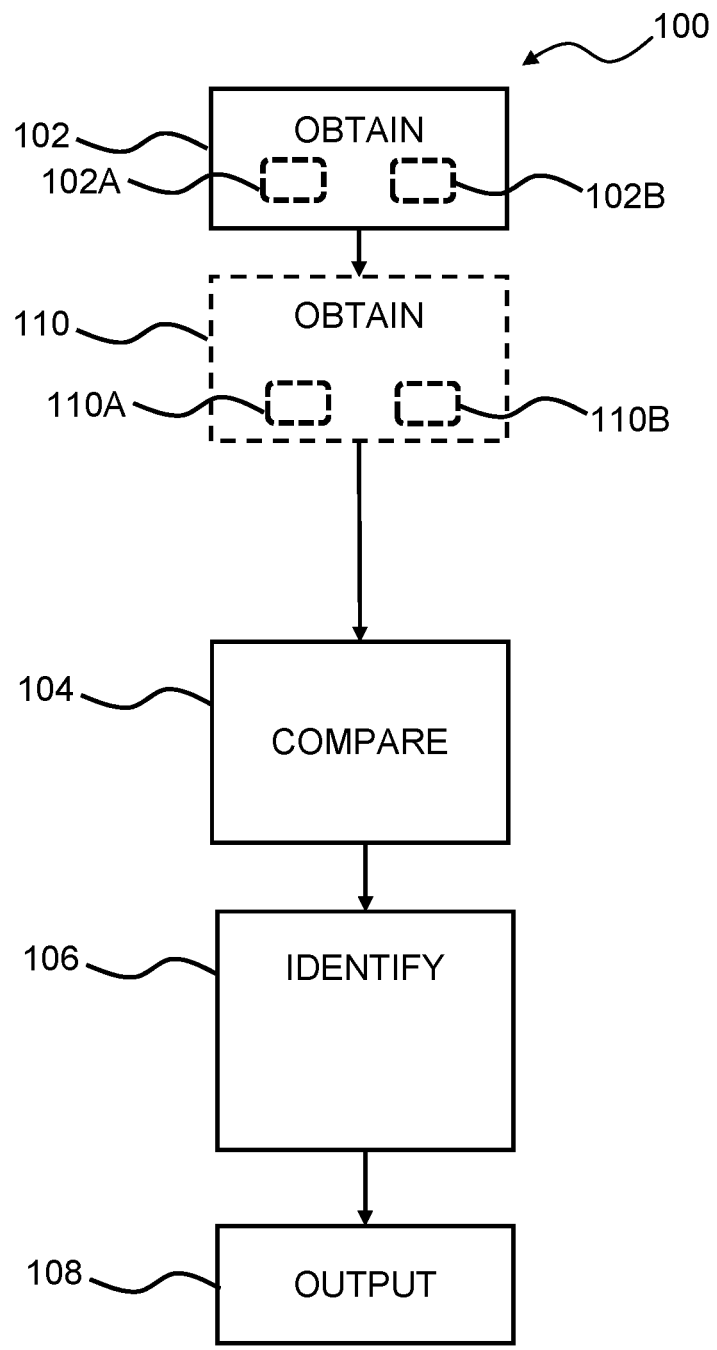
FIG. 2 is a flow diagram of an exemplary method according to the disclosure.

FIG. 2 is a flow diagram of an exemplary method according to the present disclosure. The method 100 of operating a hearing system, such as hearing system 2, comprising a first hearing device and a second hearing device is shown, the method 100 comprising obtaining 102 sensor data, the sensor data comprising first sensor data representing first physiological data and second sensor data representing second physiological data, where the first sensor data is indicative of first sensor signal from the first hearing device arranged at a first ear of a user, and the second sensor data is indicative of second sensor signal from the second hearing device arranged at a second ear of the user; comparing 104 the first sensor data and the second sensor data; identifying 106 a first parameter based on the comparison of the first sensor data and the second sensor data; and outputting 108 a first output signal indicative of the first parameter.

The method 100 optionally comprises obtaining 110 motion data comprising obtaining 110A first motion data from the first hearing device and obtaining 110B second motion data from the second hearing device. The first motion data are measured using a first motion sensor in the first hearing device and the second motion data are measured using a second motion sensor in the second hearing device. In method 100, the motion data is used as a weight factor when comparing the first sensor data and the second sensor data. In other words, the first sensor data is based on the first motion data and the second sensor data is based on the second sensor data (to form conditioned first sensor data and conditioned second sensor data).

Comparing 104 the first sensor data and the second sensor data is optionally performed in the first hearing device and/or in the accessory device. Thus, the second hearing device may transmit the second sensor data and/or one or more parameters derived from the second sensor data to the first hearing device and/or the accessory device for further analysis.

Identifying 106 a first parameter comprises performing a Heart Rate Variability analysis on the sensor data, and wherein the first parameter is indicative of heart rate variations of the user and therefore also indicative of an atrial fibrillation condition of the user. For example, a first parameter value P_1 indicating a large heart rate variation is indicative of an atrial fibrillation condition, and an atrial fibrillation condition may be detected if the first parameter P_1 meets a first criterion, e.g. if P_1>TH_1, where TH_1 is a first threshold. A first atrial fibrillation condition AFib_1 may be detected if the first parameter P_1 meets a first criterion and/or a second atrial fibrillation condition AFib_2 may be detected if the first parameter P_1 meets a second criterion.

In the method 100, the sensor data is obtained over a time period of e.g. in the range from 60 to 180 seconds, such as 120 seconds. In other words, the method preferably operates on sensor data sequences having a length in the range from 60 seconds to 180 seconds.

In one or more methods 100, the first parameter comprises a data pattern indicative of a physiological anomaly, and the first output signal is indicative of the physiological anomaly.

Figure 3:
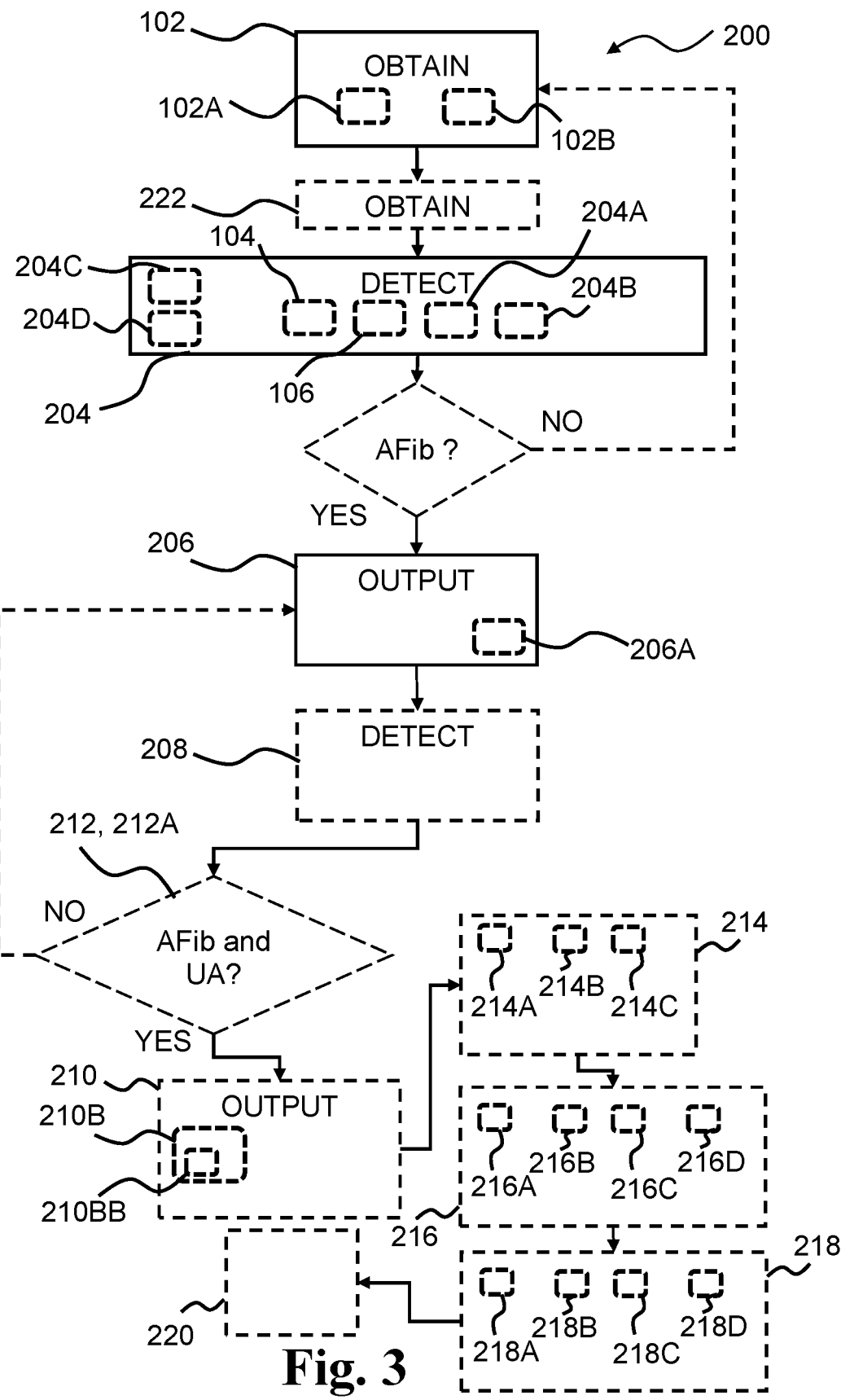
FIG. 3 is a flow diagram of an exemplary method according to the disclosure, FIG. 4 schematically illustrates an exemplary hearing device, FIG. 5 schematically illustrates processing of two PPG signals (first sensor signal and second sensor signal, and FIG. 6 illustrates an exemplary accessory device according to the disclosure

FIG. 3 is a flow diagram of an exemplary method according to the present disclosure. A method 200 of operating a hearing system, e.g. hearing system 2, comprising a first hearing device and an accessory device is shown, the method 200 comprising obtaining 102 sensor data, the sensor data comprising first sensor data indicative of a first sensor signal from the first hearing device arranged at a first ear of a user; detecting 204, e.g. in the first hearing device or in the accessory device, an atrial fibrillation condition of the user based on the first sensor data; and in accordance with detecting the atrial fibrillation condition, outputting 206 a first output signal indicative of the atrial fibrillation condition. Outputting 206 a first output signal indicative of the atrial fibrillation condition comprises outputting 206A a first audio signal via the first hearing device.

In the method 200, the hearing system comprises a second hearing device, and the sensor data comprises second sensor data indicative of a second sensor signal from the second hearing device arranged at a second ear of the user, and wherein detecting 204 an atrial fibrillation condition of the user is based on the second sensor data. In one or more exemplary methods 200, detecting 204 an atrial fibrillation condition comprises the acts of comparing 104 and identifying 106 as described in detail with reference to FIG. 2.

The method 200 comprises detecting 208 a user activation of the accessory device. User activation may be detected, when a user unlocks the accessory device, e.g. by inputting a passcode or using face ID. User activation may be detected, when a user activates a user interface element, e.g. on a home screen or a lock screen of the accessory device.

Further, the method optionally comprises outputting 210, with the accessory device, one or more output signals, e.g. in accordance 212 with one or more criteria being satisfied.

The method 200 comprises in accordance 212A with detecting the atrial fibrillation condition and detecting the user activation UA, outputting 210B a second output signal indicative of the atrial fibrillation condition. In the method 200, outputting 210B a second output signal indicative of the atrial fibrillation condition comprises displaying 210BB, on a display of the accessory device, a first user interface comprising a first user interface element indicative of the atrial fibrillation condition.

The method 200 optionally comprises 214 displaying 214A, on the display of the accessory device, a second user interface element indicative of a transmit action; detecting 214B user selection of the second user interface element; and in accordance with detecting user selection of the second user interface element, transmitting 214C the sensor data or at least parts thereof to a server device.

The method 200 optionally comprises 216 displaying 216A, on the display of the accessory device, a third user interface element indicative of a heart condition measurement with the accessory device; detecting 216B user selection of the third user interface element; in accordance with detecting user selection of the third user interface, performing 216C a heart condition measurement with the accessory device; and transmitting 216D a result of the heart condition measurement to a server device.

The method 200 optionally comprises 218 outputting 218A user instructions to the user, e.g. on display of the accessory device and/or as an audio signal via the first hearing device; detecting 218B user behaviour of the user; determining 218C if the user behaviour does not correspond to the user instructions; and in accordance with determining that the user behaviour does not correspond to the user instructions, outputting 218D a fifth output signal, e.g. on display of the accessory device and/or as an audio signal via the first hearing device, wherein the fifth output signal is indicative of non-compliance with the user instructions.

Outputting 218A user instructions to the user optionally comprises displaying, on the display of the accessory device, a fourth user interface element with user instructions, such as a text field or text box. Outputting 218A user instructions to the user optionally comprises outputting a second audio signal via the first hearing device, wherein the second audio signal is indicative of the user instructions.

In method 200, detecting 204 an atrial fibrillation condition of the user comprises performing 204A Heart Rate Variability analysis on the sensor data and determining 204B a plurality of R-R intervals based on the sensor data.

Figure 4:
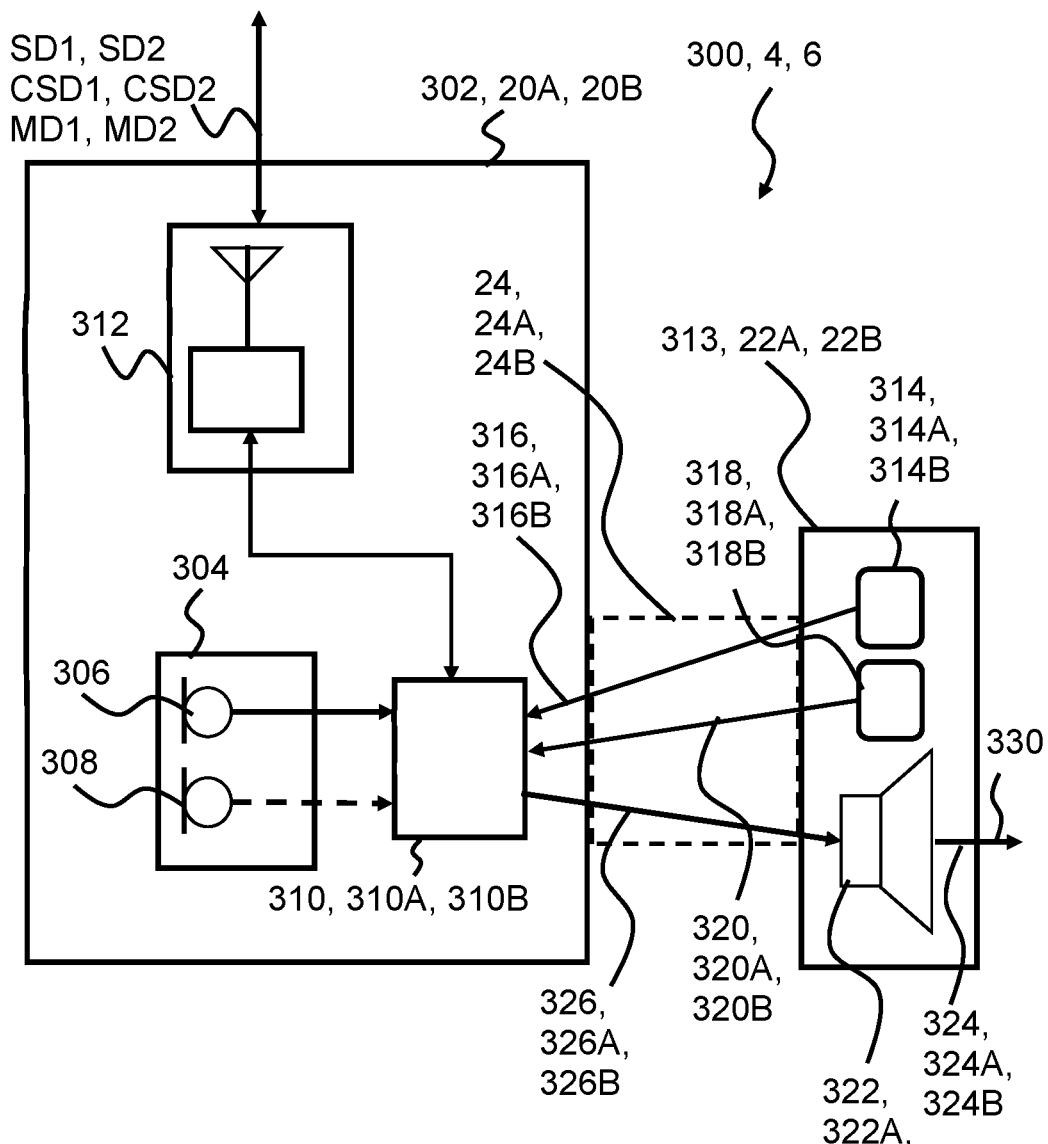

In the method 200, the first hearing device may be hearing device 4, 300 as shown in FIG. 4.

The method 200 further comprises 220 detecting a sound input signal by the first microphone for provision of a first input signal; processing by the first processor unit, the first input signal according to a hearing loss of the user wearing the first hearing device; outputting a processed signal by the first processor unit; and outputting, with the first receiver, a first audio output signal based on the processed signal.

The method 200 further comprises obtaining 222 motion data, the motion data comprising first motion data indicative of a first motion sensor signal from the motion sensor; and wherein detecting 204 an atrial fibrillation condition of the user is based on the first motion data. In method, 200, detecting 204 an atrial fibrillation condition of the user further comprises comparing 204C the first motion data to a first motion threshold; and in accordance with the first motion data satisfying a first motion criterion based on the first motion threshold, conditioning 204D the first sensor data, e.g. by weighting the first sensor data with a first weight based on the first motion data. In method, 200, comparing 204C optionally comprises comparing the second motion data to a second motion threshold; and in accordance with the second motion data satisfying a second motion criterion based on the second motion threshold, conditioning 204D the second sensor data, e.g. by weighting the second sensor data with a second weight based on the second motion data.

FIG. 4 schematically illustrates an exemplary hearing device 300, e.g. used as first hearing device 4 and/or second hearing device 6. The hearing device 300 comprises a BTE housing 302 accommodating input module 304 including first microphone 306 and optionally second microphone 308. The hearing device 300 comprises processor unit 310 accommodated or arranged in BTE housing 302. A communication unit 312 for wireless communication with accessory device, e.g. accessory device 8, and/or other hearing device is accommodated in BTE housing 302. The hearing device 300 comprises a photoplethysmogram sensor 314 (first sensor 314A for first hearing device 4, second sensor 314B for second hearing device 6) configured for providing sensor signal 316, 316A, 316B to the processor unit 310. Further, the hearing device 300 comprises a motion sensor 318 (first motion sensor 318A for first hearing device 4, second motion sensor 318B for second hearing device 6) for provision of motion data (or motion sensor signals indicative of motion data) 320, 320A, 320B to the processor unit 310. The hearing device 300 comprises a receiver 322 (first receiver 322A for first hearing device 4, second receiver 322B for second hearing device 6) for outputting an audio output signal 324 (first audio output signal 324A for first hearing device 4 and second audio output signal 324B for second hearing device 6) based on processed signal 326 from processor unit 310 (first processed signal 326A from first processor unit 310A and second processed signal from second processor unit 310B). The first sensor 314A and the second sensor 314B are configured for being positioned in the concha or in an ear canal of the user.

The first sensor 314A, the first motion sensor 318A, and the first receiver 322A are arranged or accommodated in first earpiece 22A and communicatively coupled to the BTE housing 20a via connector tube 24A comprising wires for connecting the first sensor 314A, the first motion sensor 318A, and the first receiver 322A to the first processor unit 310A. The first earpiece 22A may be a completely-in-the-canal earpiece or arranged partly in the ear canal and partly in the concha.

The first hearing device 4, is optionally configured to outputting a first output signal indicative of the atrial fibrillation condition by outputting a first audio signal 330 via the first receiver 322A of the first hearing device 4.

The first hearing device 4 may be configured to transmit first motion data MD1 and/or first sensor data SD1 to accessory device and/or second hearing device via communication module 312. The first hearing device 4 may be configured to receive control data CD via communication module 312 for control of the first hearing device 4 in accordance with sensor data and/or motion data.

The first hearing device 4 may be configured to transmit conditioned first sensor data CSD1 (first sensor data conditioned based on the first motion data) to accessory device and/or second hearing device via communication module 312.

Figure 5:
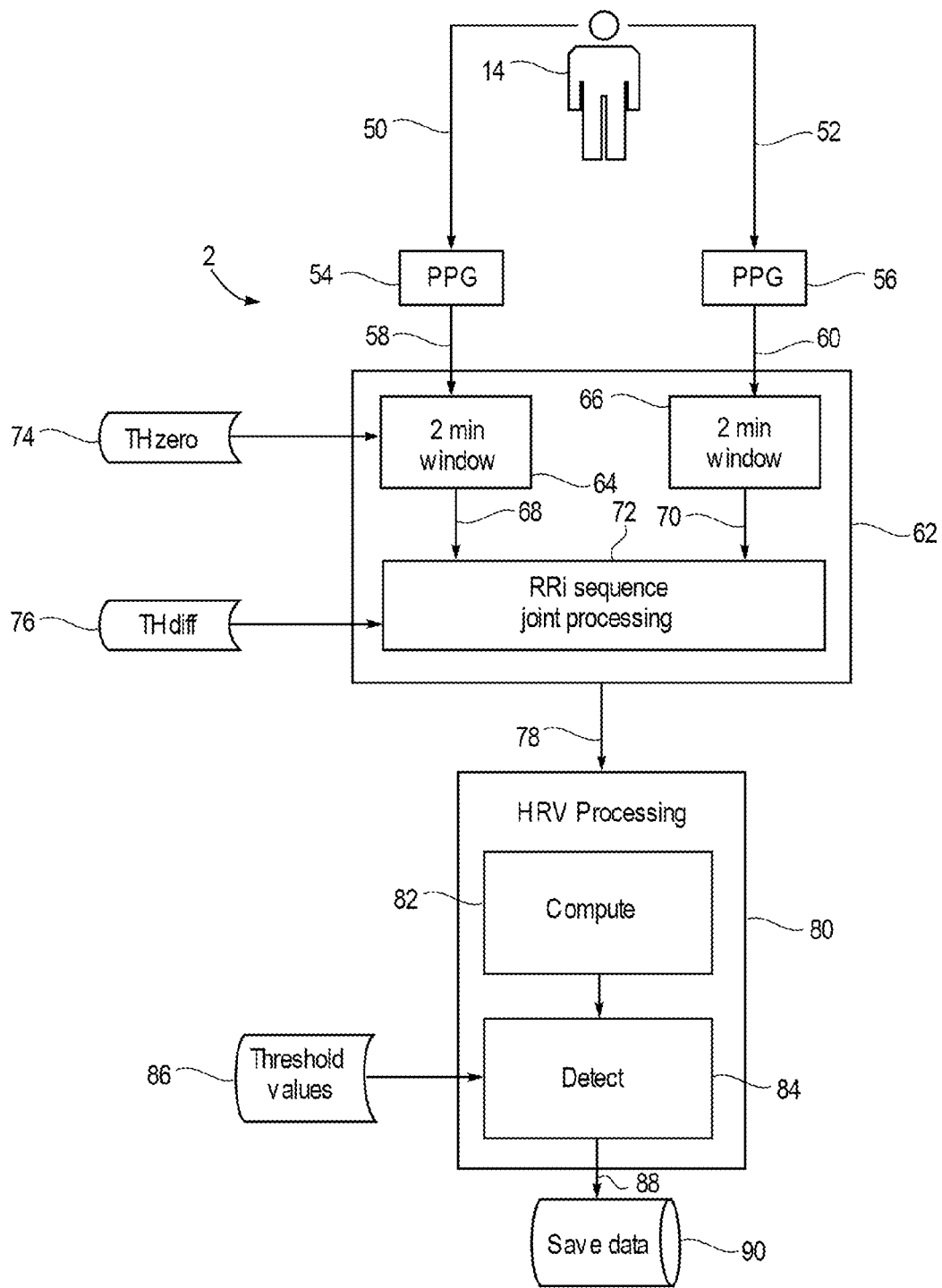

FIG. 5 schematically illustrates the processing of two PPG signals (first sensor signal 316A and second sensor signal 316B) in an embodiment of a hearing system 2 according to the present disclosure. The purpose of the processing is to produce a reliable RMSSD value of a set of RR intervals as seen over a predetermined period of time, e.g. two minutes, for the purpose of detecting a heart rate variability, which may indicate AFib. The RMSSD is the square root of the mean of the squares of differences between adjacent RR intervals in a series (period), and is a measure of variability of RR intervals. RMSSD will, in general, increase with the level of noise present in the RR tachogram, cf.:

$$RMSSD = \sqrt{\frac{1}{L-1}\sum_{j=0}^{L-1}(RRi(j+1) - RRi(j))^2} = \sqrt{\frac{1}{L-1}\sum_{j=0}^{L-1}\Delta RRi(j)^2}$$

The hearing device system 2 comprises a first hearing device 4 having a first PPG sensor 54 as first sensor 314A for collecting a first PPG stimulus 50 at a first ear of the user and a second hearing device 6 having a second PPG sensor 56 as second sensor 314B for collecting a second PPG stimulus 52 at a second ear of the user, the PPG stimuli 50, 52 being generated by changes in the blood pressure over time in the user 14. The first PPG sensor 54 generates a first PPG signal 58 (first sensor signal) as a result of the first PPG stimulus 50, and the second PPG sensor 56 generates a second PPG signal 60 (second sensor signal) as a result of the second PPG stimulus 52. The first PPG signal 58 is fed to a first RR interval window 64 of an RMSSD processor 62, and the second PPG signal 60 is fed to a second RR interval window 66 of the RMSSD processor 62. The first and the second RR interval windows 64, 66 each collect and store a set of samples of the respective RR intervals detected in the PPG signals 58, 60 measured over a two-minute period. The first RR interval window 64 compares the sampled RR intervals in the window to a stored value THzero 74 indicating the maximum allowable number of missing RR intervals in the window. If the number of sampled RR intervals present in the first window exceeds the stored value of THzero 74, the first window contents are discarded. Likewise, the second RR interval window 66 compares the sampled RR intervals in the window to the stored value of Thzero 74, and if the number of sampled RR intervals present in the second window exceeds the stored value of Thzero 74, the second window contents are discarded. If none of the PPG signals 58, 60 produce a sufficient number of RR intervals within the window period, both the first RMSSD value 68 and the second RMSSD value 70 are discarded.

The first RR interval window 64 outputs a first RR interval sequence RMSSD 68 to a first input of an RR interval sequence joint processor 72, and the second RR interval window 66 outputs a second RR interval sequence RMSSD 70 to a second input of the RR interval sequence joint processor 72. In the RR interval processor 72, the values of the first RR interval sequence RMSSD 68 (first sensor data) and the second RR interval sequence RMSSD 70 (second sensor data) are compared to a stored value THdiff 76, and the largest value is discarded if the difference between the first RR interval sequence RMSSD 68 and the second RR interval sequence RMSSD 70 exceeds THdiff 76. If the contents of the first RR interval sequence window 64 or the second RR interval sequence window 66 have been discarded, only the remaining RMSSD value is used by the RR interval sequence joint processor 72. Otherwise, the RR interval sequence joint processor 72 produces a combined RMSSD value 78 from the windowed data. By combining the RMSSD values (sensor data) from two PPG sensor signals, noise inherently present in the PPG signals may be reduced.

The combined RMSSD value 78 are processed further by a HRV (Heart Rate Variability) processor 80, where a HR (Heart Rate) value and a HRV (Heart Rate Variability) value is calculated by a HRV and HR (Heart Rate) calculator 82. These values or parameters are presented to an alarm detector 84, where they are compared to a resting HR threshold value and a HRV threshold value, respectively, from a threshold value storage 86. In combination with motion signals from the hearing devices (not shown in FIG. 5), the HR value is detected as a resting HR value and compared to the resting HR threshold. If the calculated HR value exceeds the resting HR threshold, the alarm detector 84 produces a resting HR alarm indicating an elevated resting heart rate. If the calculated HRV value exceeds the HRV threshold, an AFib detection algorithm (not shown) provides an AFib alarm.

The alarm detector 84 produces an output signal 88 as a vector comprising the time, a resting HR flag and an AFIB flag. The output signal 88 is stored in the output data storage 90 for subsequent retrieval and further analysis.

Figure 6:
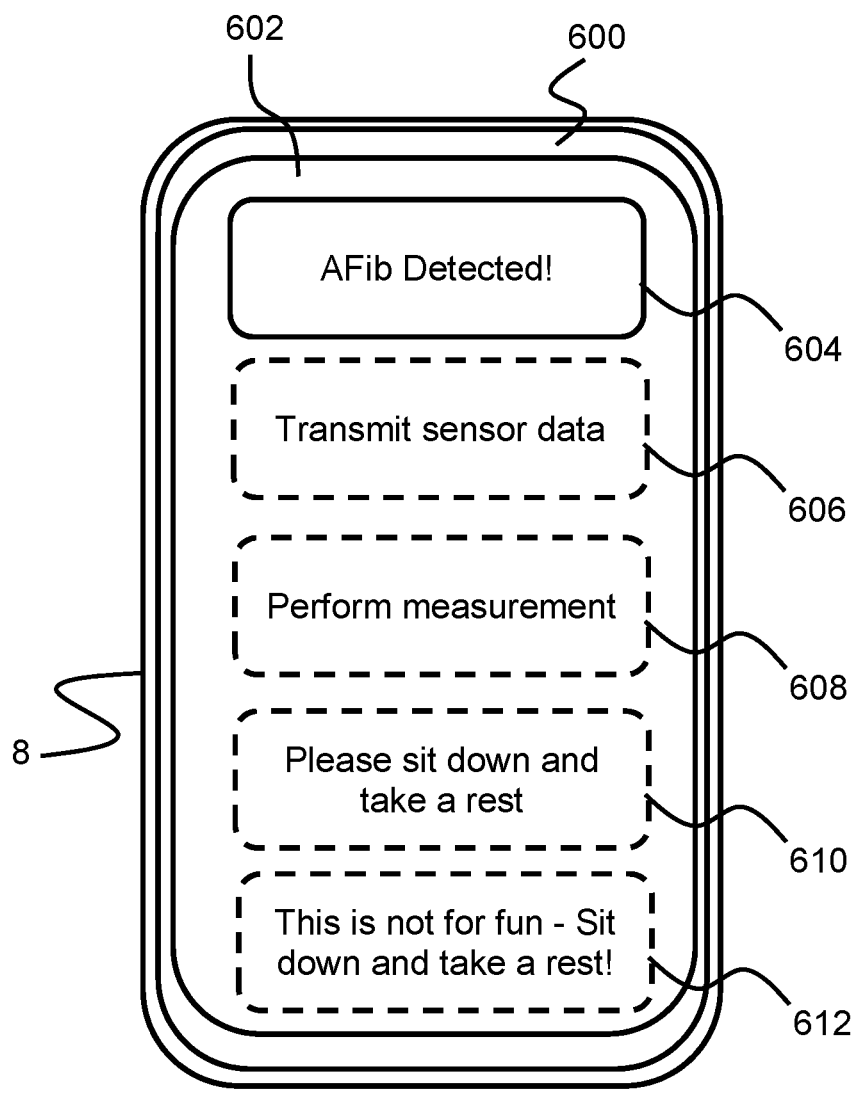

FIG. 6 shows an exemplary accessory device 8 according to the present disclosure. The accessory device 8 is optionally configured for obtaining sensor data, the sensor data comprising first sensor data and/or conditioned first sensor data from first hearing; and detecting an atrial fibrillation condition of the user based on the first sensor data. Alternatively, the accessory device is configured to obtain first control data from the first hearing device, the first control data being indicative of detection of an atrial fibrillation in the first hearing device. The accessory device 8 is configured to detect a user activation of the accessory device; and in accordance with detecting the atrial fibrillation condition and detecting the user activation, outputting a second output signal indicative of the atrial fibrillation condition. Outputting a second output signal indicative of the atrial fibrillation condition comprises displaying, on a display 600 of the accessory device 8, a first user interface 602 comprising a first user interface element 604 indicative of the atrial fibrillation condition. The first user interface element 604 may be indicative of the occurrence of atrial fibrillation condition, e.g. by comprising context data, such as a text string, e.g. "AFib detected!" as illustrated.

The accessory device 8 may be configured to display, on the display 600 of the accessory device, a second user interface element 606 indicative of a transmit action; detect user selection of the second user interface element 606; and in accordance with detecting user selection of the second user interface element 606, transmitting the sensor data or at least parts thereof to a server device. The second user interface element 606 may be displayed as part of the first user interface 602. In one or more exemplary methods/accessory devices, the second user interface element 606 may be displayed as part of a second user interface, e.g. in accordance with detecting user selection of the first user interface element 604.

The accessory device 8 may be configured to display, on the display 600 of the accessory device, a third user interface element 608 indicative of a heart condition measurement with the accessory device; detecting user selection of the third user interface element 608; and in accordance with detecting user selection of the third user interface 608, performing a heart condition measurement with the accessory device. The accessory device 8 may be configured to transmit a result of the heart condition measurement to a server device. The third user interface element 608 may be displayed as part of the first user interface 602. In one or more exemplary methods/accessory devices, the third user interface element 608 may be displayed as part of a second user interface, e.g. in accordance with detecting user selection of the first user interface element 604.

The accessory device 8 may be configured to output user instructions to the user. Output of user instructions may comprise to display, on the display of the accessory device, a fourth user interface element 610 with user instructions, such as a text field or text box. The fourth user interface element 610 may be displayed as part of the first user interface 602. In one or more exemplary methods/accessory devices, the fourth user interface element 610 may be displayed as part of a second user interface, e.g. in accordance with detecting user selection of the first user interface element 604.

The accessory device 8 may be configured to detect user behaviour of the user, e.g. with one or more motion sensors of the hearing system, and determining if the user behaviour does not correspond to the user instructions, e.g. if the user does not sit down if instructed to do so. The accessory device 8 may be configured to, in accordance with determining that the user behaviour does not correspond to the user instructions, outputting a fifth output signal indicative of non-compliance with the user instructions. Output of the fifth output signal may comprise to display, on the display of the accessory device, a fifth user interface element 612 with context data indicative of non-compliance with the user instructions, such as a text field or text box. The fifth user interface element 612 may be displayed as part of the first user interface 602. In one or more exemplary methods/accessory devices, the fifth user interface element 612 may be displayed as part of a second user interface, e.g. in accordance with detecting user selection of the first user interface element 604.

Also disclosed are method and hearing systems according to any of the following items and articles.

Item 1. A method of operating a hearing system comprising a first hearing device and an accessory device, the method comprising:
   obtaining sensor data, the sensor data comprising first sensor data indicative of a first sensor signal from the first hearing device arranged at a first ear of a user;
   detecting an atrial fibrillation condition of the user based on the first sensor data; and
   in accordance with detecting the atrial fibrillation condition, outputting a first output signal indicative of the atrial fibrillation condition.

Item 2. Method according to item 1, the hearing system comprising a second hearing device, wherein the sensor data comprises second sensor data indicative of a second sensor signal from the second hearing device arranged at a second ear of the user, and wherein detecting an atrial fibrillation condition of the user is further based on the second sensor data.

Item 3. Method according to any one of items 1-2, wherein outputting a first output signal indicative of the atrial fibrillation condition comprises outputting a first audio signal via the first hearing device.

Item 4. Method according to any one of items 1-3, the method comprising detecting a user activation of the accessory device; and in accordance with detecting the atrial fibrillation condition and detecting the user activation, outputting a second output signal indicative of the atrial fibrillation condition.

Item 5. Method according to item 4, wherein outputting a second output signal indicative of the atrial fibrillation condition comprises displaying, on a display of the accessory device, a first user interface comprising a first user interface element indicative of the atrial fibrillation condition.

Item 6. Method according to any one of items 4-5, wherein the method comprises displaying, on the display of the accessory device, a second user interface element indicative of a transmit action; detecting user selection of the second user interface element; and in accordance with detecting user selection of the second user interface element, transmitting the sensor data to a server device.

Item 7. Method according to any one of items 4-6, wherein the method comprises displaying, on the display of the accessory device, a third user interface element indicative of a heart condition measurement with the accessory device; detecting user selection of the third user interface element; and in accordance with detecting user selection of the third user interface, performing a heart condition measurement with the accessory device.

Item 8. Method according to item 7, the method comprising transmitting a result of the heart condition measurement to a server device.

Item 9. Method according to any one of items 4-8, wherein the method comprises outputting user instructions to the user; detecting user behaviour of the user; determining if the user behaviour does not correspond to the user instructions; and in accordance with determining that the user behaviour does not correspond to the user instructions, outputting a fifth output signal indicative of non-compliance with the user instructions.

Item 10. Method according to any one of items 1-9, wherein detecting an atrial fibrillation condition of the user comprises performing Heart Rate Variability analysis on the sensor data.

Item 11. Method according to any one of items 1-10, wherein detecting an atrial fibrillation condition of the user comprises determining a plurality of R-R intervals based on the sensor data.

Item 12. Method according to any one of items 1-11, wherein a first sensor providing the first sensor signal is a photoplethysmogram sensor.

Item 13. Method according to any one of items 1-12 as dependent on item 2, wherein a second sensor providing the second sensor signal is a photoplethysmogram sensor.

Item 14. Method according to any one of items 1-13, wherein the first hearing device comprises a first microphone and a first processor unit, wherein the method further comprises:

detecting a sound input signal by the first microphone for provision of a first input signal;

processing by the first processor unit, the first input signal according to a hearing loss of the user wearing the first hearing device; and outputting a processed signal by the first processor unit.

Item 15. Method according to item 14, wherein the hearing system further comprises a first receiver, wherein the method further comprises:

outputting, with the first receiver, a first audio output signal based on the processed signal.

Item 16. Method according to any one of items 1-15, wherein the hearing system comprises a first sensor configured for providing the first sensor signal.

Item 17. Method according to item 16, wherein the first sensor is configured for being positioned in the concha or in an ear canal of the user.

Item 18. Method according to item 16 or 17, wherein the first sensor is communicatively coupled to the first hearing device/first processor unit via a second cable comprising a plurality of electrical wires.

Item 19. Method according to anyone of items 15 or 16-18 as dependent on item 15, wherein the first receiver is positioned at least partly in an ear canal of the user, and wherein the first receiver is communicatively coupled to the first hearing device/first processor unit via a first cable comprising a plurality of electrical wires.

Item 20. Method according to anyone of items 1-19, wherein the first hearing device comprises a motion sensor, and wherein the method further comprises:

obtaining motion data, the motion data comprising first motion data indicative of a first motion sensor signal from the motion sensor; and wherein detecting an atrial fibrillation condition of the user is based on the first motion data.

Item 21. Method according to item 20, wherein detecting an atrial fibrillation condition of the user further comprises:

comparing the first motion data to a first motion threshold; and in accordance with the first motion data satisfying a first motion criterion based on the first motion threshold, conditioning the first sensor data.

Item 22. Method according to item 16 when dependent on claim 15, wherein the first receiver and the first sensor are contained in a housing in the ear canal of the user.

Item 23. Hearing system comprising a first hearing device and an accessory device, wherein the hearing system is configured to perform a method according to any of items 1-22.

Article 1. A method of operating a hearing system comprising a first hearing device and a second hearing device, the method comprising:

obtaining sensor data, the sensor data comprising first sensor data representing first physiological data and second sensor data representing second physiological data, where the first sensor data is indicative of first sensor signal from the first hearing device arranged at a first ear of a user, and the second sensor data is indicative of second sensor signal from the second hearing device arranged at a second ear of the user;

comparing the first sensor data and the second sensor data;

identifying a first parameter based on the comparison of the first sensor data and the second sensor data; and outputting a first output signal indicative of the first parameter.

Article 2. Method according to article 1, where the method further comprises obtaining motion data from the first hearing device and/or the second hearing device.

Article 3. Method according to article 2, wherein comparing the first sensor data and the second sensor data is based on the motion data.

Article 4. Method according to any one of articles 2 or 3, wherein the motion data is measured using a motion sensor arranged in the first hearing device or in the second hearing device.

Article 5. Method according to any one of articles 1-4, wherein the first physiological data and the second physiological data is representative of a heart function of a user.

Article 6. Method according to any one of articles 1-5, wherein the first parameter is indicative of heart rate variations of the user.

Article 7. Method according to any one of articles 1-5, wherein the method comprises
identifying a second parameter based on the first sensor data, the second sensor data and the first parameter, wherein the second parameter is indicative of presence of atrial fibrillation.

Article 8. Method according to any one of articles 1-5, wherein the first parameter is indicative of an atrial fibrillation condition of the user.

Article 9. Method according to any one of articles 1-8, wherein comparing the first sensor data and the second sensor data is performed in the first hearing device.

Article 10. Method according to any one of articles 1-9, where the first sensor data is obtained via a first sensor of the first hearing device and/or the second sensor data is obtained via a second sensor of the second hearing device.

Article 11. Method according to any one of articles 1-10, wherein the sensor data is obtained over a time period of more than 30 seconds, preferably more than 60 seconds, preferably more than 90 seconds, preferably 120 seconds.

Article 12. Method according to any one of articles 1-11, wherein identifying the first parameter comprises identifying parts of the sensor data that differ from default physiological data.

Article 13. Method according to any one of articles 1-12, wherein identifying the first parameter comprises identifying parts of the sensor data that have a similarity to a predefined pattern representing a physiological anomaly.

Article 14. Method according to any one of articles 1-12, wherein identifying a first parameter comprises identifying periods of the first and the second sensor data, respectively, comparing periods of the first and the second sensor data, and identifying the first parameter based on the periods of the first and the second sensor data Article 15. Method according to any one of articles 1-14, wherein the first parameter comprises a data pattern.

Article 16. Method according to article 15, wherein the data pattern is indicative of a physiological anomaly.

Article 17. Method according to any one of articles 1-16, wherein identifying the first parameter comprises performing a Heart Rate Variability analysis on the sensor data.

Article 18. Method according to any one of articles 1-16, wherein the first parameter is indicative of one or more R-R intervals of the sensor data.

Article 19. Method according to any one of articles 1-18, wherein a first sensor providing the first sensor signal is a photoplethysmogram sensor, and wherein a second sensor providing the second sensor signal is a photoplethysmogram sensor.

Article 20. Hearing system comprising:
a first hearing device comprising a first sensor for obtaining first sensor data;
a second hearing device comprising a second sensor for obtaining second sensor data;
a processing unit configured to:
compare the first sensor data and the second sensor data;
identify a first parameter based on the comparison of the first sensor data and the second data; and
output a first output signal indicative of the first parameter.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-3 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, agents, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 hearing system
4 first hearing device
6 second hearing device
8 accessory device
9 server device
10 wireless connection
12 wireless connection
13 wireless connection
13A connection from accessory device to server device
14 user
16 first ear
18 second ear
20 behind-the-ear housing
20A first behind-the-ear housing
20B second behind-the-ear housing
22 earpiece
22A first earpiece
22B second earpiece
24 tube connector
24A first tube connector
24B second tube connector
50 first PPG stimulus
52 second PPG stimulus
54 first PPG sensor
56 second PPG sensor
58 first PPG signal
60 second PPG signal
62 RMSSD processor
64 first 120-second RR interval window
66 second 120-second RR interval window
68 first RR interval sequence RMSSD
70 second RR interval sequence RMSSD
72 RR interval sequence joint processor
74 THZero—max allowable number of missing RR intervals in window/period
76 THdiff—max allowable difference between left and right RMSSD before discarding largest
78 combined RMSSD signal
80 HRV (Heart Rate Variability) processor
82 HRV and HR (Heart Rate) calculator
84 alarm detector
86 threshold value storage
88 output signal
90 output data storage
100 method of operating a hearing system comprising a first hearing device and a second hearing device
102 obtaining sensor data
102A obtaining first sensor data
102B obtaining second sensor data
104 comparing the first sensor data and the second sensor data
106 identifying a first parameter
108 outputting a first output signal
110 obtain motion data
110A obtain first motion data
110B obtain second motion data
200 operating a hearing system comprising a first hearing device and an accessory device
204 detecting an atrial fibrillation condition
204A performing Heart Rate Variability analysis on the sensor data
204B determining a plurality of R-R intervals based on the sensor data
204C comparing the motion data to motion threshold(s)
204D conditioning the sensor data
206 outputting a first output signal
206A outputting a first audio signal via the first hearing device
208 detecting a user activation of the accessory device
210 outputting, with the accessory device, one or more output signals
210B outputting a second output signal indicative of the atrial fibrillation condition
210BB displaying, on a display of the accessory device, a first user interface comprising a first user interface element indicative of the atrial fibrillation condition
212 in accordance with one or more criteria being satisfied
212A in accordance with detecting the atrial fibrillation condition and detecting the user activation
214A displaying, on the display of the accessory device, a second user interface element indicative of a transmit action
214B detecting user selection of the second user interface element
214C transmitting the sensor data to a server device
216A displaying, on the display of the accessory device, a third user interface element indicative of a heart condition measurement with the accessory device
216B detecting user selection of the third user interface element
216C performing a heart condition measurement with the accessory device
216D transmitting a result of the heart condition measurement to a server device.
218A outputting user instructions to the user
218B detecting user behaviour of the user
218C determining if the user behaviour does not correspond to the user instructions
218D outputting a fifth output signal indicative of non-compliance with the user instructions
220 hearing aid operations
222 obtaining motion data
300 hearing device
302 BTE housing
304 input module
306 first microphone
308 second microphone
310 processor unit
310A first processor unit of first hearing device
310B second processor unit of second hearing device
312 communication module
314 sensor
314A first sensor of first hearing device
314B second sensor of second hearing device 316 sensor signal
316A first sensor signal from first sensor
316B second sensor signal from second sensor
318 motion sensor
318A first motion sensor of first hearing device
318B second motion sensor of second hearing device
320, MD motion data
320A, MD1 first motion data
320B, MD2 second motion data
322 receiver
322A first receiver of first hearing device
322B second receiver of second hearing device
324 audio output signal
324A first audio output signal from first hearing device
324B second audio output signal from second hearing device
326 processed signal from processor unit
326A first processed signal from first processor unit
326B second processed signal from second processor unit
330 first audio signal from first hearing device and/or from second hearing device
600 display of accessory device
602 first user interface
604 first user interface element
606 second user interface element
608 third user interface element
610 fourth user interface element
612 fifth user interface element
SD1 first sensor data
SD2 second sensor data
CSD1 conditioned first sensor data
CSD2 conditioned second sensor data

The invention claimed is:

1. A hearing device comprising:
 a first microphone configured to provide a first input signal;
 a first processor unit configured to provide a processed signal based on the first input signal to compensate for a hearing loss of a user of the first hearing device;
 a receiver configured to output sound based on the processed signal; and
 a first sensor configured to provide a first sensor signal for detecting an atrial fibrillation condition of the user;
 wherein the hearing device is configured to process the first sensor signal to detect the atrial fibrillation condition of the user;
 wherein the hearing device is configured to detect the atrial fibrillation condition based on a first-stage processing and a second-stage processing, wherein in the first-stage processing, the hearing device is configured to determine a square-root of a mean of squares of differences between adjacent RR intervals in the first sensor signal, and wherein in the second-stage processing, the hearing device is configured to determine a heart rate variability based on the square-root of the mean of the squares of differences, and compare the heart rate variability with a heart rate variability threshold.

2. The hearing device according to claim 1, wherein the receiver is configured to output an audio signal indicative of the atrial fibrillation condition.

3. The hearing device according to claim 1, further comprising a communication unit configured to transmit first sensor data away from the hearing device, the first sensor data being based on the first sensor signal.

4. The hearing device according to claim 1, comprising an earpiece, wherein the receiver and the first sensor are at the earpiece.

5. The hearing device according to claim 4, further comprising a unit located outside the earpiece, wherein the unit is coupled to the earpiece via a cable, wherein the processing unit is at the unit, and wherein the unit comprises a detector configured to detect the atrial fibrillation condition of the user based on the first sensor signal.

6. The hearing device according to claim 4, wherein at least a part of the earpiece is configured for placement in an ear canal of the user.

7. The hearing device according to claim 4, further comprising a detector in the earpiece, wherein the detector is configured to detect the atrial fibrillation condition of the user based on the first sensor signal.

8. The hearing device according to claim 1, wherein the first sensor is configured for placement in an ear canal of the user.

9. The hearing device according to claim 1, wherein the first sensor is configured for placement at a concha of the user.

10. The hearing device according to claim 1, further comprising a motion sensor configured to provide a first motion sensor signal.

11. The hearing device according to claim 10, further comprising a detector configured to detect the atrial fibrillation condition of the user based on the first motion sensor signal.

12. The hearing device according to claim 11, wherein the detector is configured to detect the atrial fibrillation condition of the user based on a comparison between the first motion data and a first motion threshold.

13. The hearing device of claim 10, wherein the hearing device is configured to determine whether a behavior of the user satisfies a criterion based on the first motion sensor signal.

14. The hearing device of claim 13, wherein the hearing device is configured to determine whether the behavior of the user satisfies the criterion by determining whether the behavior of the user corresponds with an instructed task based on the first motion sensor signal.

15. The hearing device according to claim 1, further comprising a detector configured to detect the atrial fibrillation condition of the user based on the first sensor signal, the detector comprising the first-stage processing and the second-stage processing.

16. A hearing system comprising the hearing device of claim 1, and an additional hearing device, wherein the additional hearing device comprises a second sensor configured to provide a second sensor signal for detecting the atrial fibrillation condition of the user.

17. A hearing system comprising the hearing device of claim 1, and an accessory device.

18. The hearing system of claim 17, wherein the accessory device is configured to output a signal indicative of the atrial fibrillation condition.

19. The hearing system according to claim 17, wherein the accessory device is configured to output the signal by displaying, on a display of the accessory device, a user interface element indicative of the atrial fibrillation condition.

20. The hearing system according to claim 17, wherein the accessory device is configured to display a user interface element indicative of a transmit action; and wherein the accessory device is configured to transmit data associated with the first sensor signal to a server device after the user interface element has been selected.

21. An electronic device, comprising:
a communication interface configured to communicate with a hearing device that is configured to be worn by a user of the electronic device; and
a processing unit;
wherein the processing unit is configured to obtain, via the communication interface, a sensor data transmitted from the hearing device;
wherein the processing unit is configured to detect an atrial fibrillation condition of the user by obtaining a square-root of a mean of squares of differences between adjacent RR intervals in the sensor data, determining a heart rate variability based on the square-root of the mean of the squares of differences, and comparing the heart rate variability with a heart rate variability threshold; and
wherein the electronic device is configured to output a signal indicative of the atrial fibrillation condition.

22. The electronic device according to claim 21, wherein the processing unit of the electronic device comprises a detector configured to detect the atrial fibrillation condition based on the sensor data.

23. The electronic device according to claim 21, further comprising a display configured to output the signal indicative of the atrial fibrillation condition.

24. The electronic device according to claim 23, wherein the display of the electronic device is configured to display a user interface element indicative of a transmit action; and
wherein the electronic device is configured to transmit data associated with the first sensor data to a server device after the user interface element has been selected.

25. The electronic device according to claim 23, wherein the display of the electronic device is configured to display a user interface element indicative of a measurement action to measure a heart condition; and
wherein the electronic device is configured to perform a heart condition measurement after the user interface element has been selected.

26. The electronic device of claim 21, wherein the electronic device is configured to instruct the user to perform a task, and wherein the processing unit is configured to determine whether the behavior of the user satisfies a criterion by determining whether the behavior of the user corresponds with the task based on the motion data.

27. A method performed by a hearing system comprising a first hearing device configured to be worn by a user and/or an accessory device, the method comprising:
providing sensor data, the sensor data comprising first sensor data indicative of a first sensor signal from a first sensor of the first hearing device arranged at a first ear of the user;
detecting, by the hearing system, an atrial fibrillation condition of the user, wherein the detecting the atrial fibrillation comprises obtaining a square-root of a mean of squares of differences between adjacent RR intervals in the sensor data, determining a heart rate variability based on the square-root of the mean of the squares of differences, and comparing the heart rate variability with a heart rate variability threshold; and
outputting, by the hearing system, a first output signal indicative of the detected atrial fibrillation condition.

28. The method according to claim 27, wherein the hearing system comprises a second hearing device, wherein the sensor data comprises second sensor data indicative of a second sensor signal from a second sensor of the second hearing device arranged at a second ear of the user, and wherein the act of detecting the atrial fibrillation condition of the user is performed also based on the second sensor data.

29. The method according to claim 27, wherein the first output signal is output via the first hearing device, and wherein the first output signal comprises a first audio signal.

30. The method according to claim 27, wherein the hearing system also comprises an accessory device, and wherein the method further comprises:
detecting a user activation of the accessory device; and
outputting a second output signal indicative of the detected atrial fibrillation condition.

31. The method according to claim 30, wherein the act of outputting the second output signal indicative of the detected atrial fibrillation condition comprises displaying, on a display of the accessory device, a user interface element indicative of the detected atrial fibrillation condition.

32. The method according to claim 30, further comprising:
displaying, on the display of the accessory device, a user interface element indicative of a transmit action;
detecting a user selection of the user interface element; and
in accordance with the detected user selection of the user interface element, transmitting the sensor data to a server device.

33. The method according to claim 30, further comprising:
displaying, on the display of the accessory device, a user interface element indicative of a measurement action to measure a heart condition;
detecting a user selection of the user interface element; and
in accordance with the detected user selection of the user interface, performing a heart condition measurement with the accessory device.

34. The method according to claim 30, further comprising:
outputting, by the accessory device, user instruction to the user;
detecting user behavior of the user;
outputting a signal indicative of non-compliance with the user instruction if the user behavior does not correspond to the user instruction.

35. The method according to claim 27, wherein the first hearing device comprises a first microphone, a first processor unit, and a first receiver, and wherein the method further comprises:
detecting a sound input signal by the first microphone for provision of a first input signal;
providing, by the first processor unit, a processed signal based on the first input signal to compensate for a hearing loss of the user; and
outputting, by the first receiver, a first audio output signal based on the processed signal.

36. The method according to claim 27, wherein the act of detecting the atrial fibrillation condition of the user based on the first sensor data is performed by a processing unit in the first hearing device.

37. The method according to claim 27, wherein the first sensor is at an earpiece of the first hearing device, and wherein the earpiece is coupled to a behind-the-ear unit via a first cable comprising a plurality of electrical wires.

38. The method according to claim 27, wherein the first hearing device comprises a motion sensor, and wherein the method further comprises:
 obtaining motion data, the motion data comprising first motion data indicative of a first motion sensor signal from the motion sensor;
 wherein the atrial fibrillation condition of the user is detected based also on the first motion data.

39. The method according to claim 38, wherein the atrial fibrillation condition of the user is detected based on a comparison between the first motion data and a first motion threshold.

40. The method according to claim 38, further comprising conditioning the first sensor data if the first motion data satisfies a first motion criterion.

41. The method of claim 38, further comprising determining whether a behavior of the user satisfies a criterion based on the motion data.

42. The method of claim 41, wherein the behavior of the user is considered as satisfying the criterion when the behavior of the user corresponds with an instructed task as indicated by the motion data.

43. A hearing system configured to perform the method according to claim 27.

* * * * *